United States Patent
Li et al.

(10) Patent No.: US 8,694,129 B2
(45) Date of Patent: Apr. 8, 2014

(54) DEPLOYABLE SENSOR PLATFORM ON THE LEAD SYSTEM OF AN IMPLANTABLE DEVICE

(75) Inventors: Dan Li, Shoreview, MN (US); Allan C. Shuros, St. Paul, MN (US); Andrea Acuna, Miami, FL (US); Bruce A. Tockman, Scandia, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 374 days.

(21) Appl. No.: 12/686,050

(22) Filed: Jan. 12, 2010

(65) Prior Publication Data

US 2010/0210923 A1 Aug. 19, 2010

Related U.S. Application Data

(60) Provisional application No. 61/152,486, filed on Feb. 13, 2009.

(51) Int. Cl.
*A61B 5/02* (2006.01)

(52) U.S. Cl.
USPC ........... 607/122; 600/372; 600/373; 600/377; 607/115; 607/116

(58) Field of Classification Search
USPC .............. 600/300, 372–373, 377, 381; 606/1, 606/129; 607/1–2, 115, 116, 122
See application file for complete search history.

(56) References Cited

U.S. PATENT DOCUMENTS

| | | | |
|---|---|---|---|
| 3,874,388 A | 4/1975 | King et al. | |
| 4,391,124 A | 7/1983 | Drost et al. | |
| 4,407,296 A | 10/1983 | Anderson | |
| 4,485,813 A | 12/1984 | Anderson et al. | |
| 4,492,107 A | 1/1985 | Sandhu | |
| 4,672,976 A | 6/1987 | Kroll | |
| 4,836,204 A | 6/1989 | Landymore et al. | |
| 4,846,191 A | 7/1989 | Brockway et al. | |

(Continued)

FOREIGN PATENT DOCUMENTS

| | | |
|---|---|---|
| EP | 0 897 690 | 2/1999 |
| EP | 0 928 598 | 8/2000 |

(Continued)

OTHER PUBLICATIONS

Goodall, Eleanor V. et al., "Position-Selective Activation of Peripheral Nerve Fibers with a Cuff Electrode", IEEE Transactions on Biomedical Engineering, IEEE Service Center, Piscataway, NJ, US, vol. 43, No. 8, Aug. 1, 1996.

(Continued)

*Primary Examiner* — Deborah Malamud

(74) *Attorney, Agent, or Firm* — Faegre Baker Daniels LLP

(57) ABSTRACT

Systems and methods for deploying a sensor assembly onto a cardiac lead are disclosed. The sensor assembly can include a resilient cuff having one or more sensor modules for sensing physiological parameters within the body. The resilient cuff may have a substantially cylindrical shape having an inner diameter that is smaller than an outer diameter of the lead body onto which the cuff is deployed such that the cuff is retained on the lead body by frictional forces. The sensor assembly may be deployed in conjunction with a new lead to be implanted within a chamber of the patient's heart or a body vessel, or may be deployed onto an existing, implanted lead implanted within the patient's body.

18 Claims, 6 Drawing Sheets

(56) References Cited

U.S. PATENT DOCUMENTS

| | | |
|---|---|---|
| 4,900,303 A | 2/1990 | Lemelson |
| 4,917,089 A | 4/1990 | Sideris |
| 4,966,148 A | 10/1990 | Millar |
| 5,040,538 A | 8/1991 | Mortazavi |
| 5,218,965 A | 6/1993 | Ring |
| 5,284,138 A | 2/1994 | Kujawski |
| 5,303,207 A | 4/1994 | Brady et al. |
| 5,334,217 A | 8/1994 | Das |
| 5,411,551 A | 5/1995 | Winston et al. |
| 5,415,630 A | 5/1995 | Gory et al. |
| 5,451,235 A | 9/1995 | Lock et al. |
| 5,604,531 A | 2/1997 | Iddan et al. |
| 5,634,936 A | 6/1997 | Linden et al. |
| 5,656,036 A | 8/1997 | Palmaz |
| 5,662,711 A | 9/1997 | Douglas |
| 5,704,352 A | 1/1998 | Tremblay et al. |
| 5,725,552 A | 3/1998 | Kotula et al. |
| 5,733,313 A | 3/1998 | Barreras, Sr. et al. |
| 5,772,669 A | 6/1998 | Vrba |
| 5,775,331 A | 7/1998 | Raymond et al. |
| 5,800,497 A | 9/1998 | Bakels et al. |
| 5,824,053 A | 10/1998 | Khosravi et al. |
| 5,833,603 A | 11/1998 | Kovacs et al. |
| 5,855,563 A | 1/1999 | Kaplan et al. |
| 5,860,923 A | 1/1999 | Lenker et al. |
| 5,891,154 A | 4/1999 | Loeffler |
| 5,967,980 A | 10/1999 | Ferre et al. |
| 5,967,986 A | 10/1999 | Cimochowski et al. |
| 5,967,989 A | 10/1999 | Cimochowski et al. |
| 5,995,876 A | 11/1999 | Kruse et al. |
| 6,002,969 A | 12/1999 | Machek et al. |
| 6,015,386 A | 1/2000 | Kensey et al. |
| 6,015,387 A | 1/2000 | Schwartz et al. |
| 6,030,413 A | 2/2000 | Lazarus |
| 6,033,366 A | 3/2000 | Brockway et al. |
| 6,053,873 A | 4/2000 | Govari et al. |
| 6,076,016 A | 6/2000 | Feierbach |
| 6,077,227 A * | 6/2000 | Miesel et al. ............ 600/486 |
| 6,097,984 A | 8/2000 | Douglas |
| 6,106,464 A | 8/2000 | Bass et al. |
| 6,140,740 A | 10/2000 | Porat et al. |
| 6,159,156 A | 12/2000 | Van Bockel |
| 6,179,858 B1 | 1/2001 | Squire et al. |
| 6,193,745 B1 | 2/2001 | Fogarty et al. |
| 6,214,025 B1 | 4/2001 | Thistle et al. |
| 6,231,516 B1 | 5/2001 | Keilman |
| 6,236,889 B1 | 5/2001 | Soykan et al. |
| 6,239,724 B1 | 5/2001 | Doron et al. |
| 6,240,312 B1 | 5/2001 | Alfano et al. |
| 6,246,898 B1 | 6/2001 | Vesely et al. |
| 6,277,078 B1 | 8/2001 | Porat et al. |
| 6,278,790 B1 | 8/2001 | Davis et al. |
| 6,309,350 B1 | 10/2001 | VanTassel |
| 6,328,699 B1 | 12/2001 | Eigler et al. |
| 6,331,163 B1 | 12/2001 | Kaplan |
| 6,379,308 B1 | 4/2002 | Brockway et al. |
| 6,409,674 B1 | 6/2002 | Brockway et al. |
| 6,416,474 B1 | 7/2002 | Penner et al. |
| 6,432,050 B1 | 8/2002 | Porat et al. |
| 6,442,413 B1 | 8/2002 | Silver |
| 6,447,522 B2 | 9/2002 | Gambale et al. |
| 6,475,170 B1 | 11/2002 | Doron et al. |
| 6,486,588 B2 | 11/2002 | Doron et al. |
| 6,527,780 B1 | 3/2003 | Wallace et al. |
| 6,543,272 B1 | 4/2003 | Vitek |
| 6,585,763 B1 | 7/2003 | Keilman et al. |
| 6,592,553 B2 | 7/2003 | Zhang et al. |
| 6,628,989 B1 | 9/2003 | Penner et al. |
| 6,645,143 B2 | 11/2003 | VanTassel et al. |
| 6,660,021 B1 | 12/2003 | Palmer et al. |
| 6,685,638 B1 | 2/2004 | Taylor et al. |
| 6,689,056 B1 | 2/2004 | Kilcoyne et al. |
| 6,699,186 B1 | 3/2004 | Wolinsky et al. |
| 6,702,847 B2 | 3/2004 | DiCarlo |
| 6,730,108 B2 | 5/2004 | Van Tassel et al. |
| 6,738,671 B2 | 5/2004 | Christophersom et al. |
| 6,743,173 B2 | 6/2004 | Penner et al. |
| 6,746,404 B2 | 6/2004 | Schwartz |
| 6,747,916 B1 | 6/2004 | Fleury et al. |
| 6,755,855 B2 | 6/2004 | Yurek et al. |
| 6,764,446 B2 | 7/2004 | Wolinsky et al. |
| 6,783,499 B2 | 8/2004 | Schwartz |
| 6,800,060 B2 | 10/2004 | Marshall |
| 6,840,956 B1 | 1/2005 | Wolinsky et al. |
| 6,855,115 B2 | 2/2005 | Fonseca et al. |
| 6,868,288 B2 | 3/2005 | Thompson |
| 6,890,303 B2 | 5/2005 | Fitz |
| 6,899,729 B1 | 5/2005 | Cox |
| 6,904,308 B2 | 6/2005 | Frisch et al. |
| 6,920,347 B2 | 7/2005 | Simon et al. |
| 6,926,670 B2 | 8/2005 | Rich |
| 6,934,573 B1 | 8/2005 | Glukhovsky et al. |
| 6,950,690 B1 | 9/2005 | Meron et al. |
| 6,958,034 B2 | 10/2005 | Iddan |
| 6,970,742 B2 | 11/2005 | Mann et al. |
| 6,972,017 B2 | 12/2005 | Smith et al. |
| 6,984,205 B2 | 1/2006 | Gazdzinski |
| 7,001,329 B2 | 2/2006 | Kobayashi et al. |
| 7,006,858 B2 | 2/2006 | Silver et al. |
| 7,009,634 B2 | 3/2006 | Iddan et al. |
| 7,011,671 B2 | 3/2006 | Welch |
| 7,024,248 B2 | 4/2006 | Penner et al. |
| 7,033,322 B2 | 4/2006 | Silver |
| 7,035,684 B2 | 4/2006 | Lee |
| 7,039,453 B2 | 5/2006 | Mullick et al. |
| 7,060,038 B2 | 6/2006 | Letort et al. |
| 7,064,472 B2 | 6/2006 | Peline et al. |
| 7,065,409 B2 | 6/2006 | Mazar |
| 7,076,305 B2 | 7/2006 | Imran et al. |
| 7,083,822 B2 | 8/2006 | Brightbill |
| 7,116,352 B2 | 10/2006 | Yaron |
| 7,118,529 B2 | 10/2006 | Glukhovsky et al. |
| 7,118,531 B2 | 10/2006 | Krill |
| 7,131,986 B2 | 11/2006 | Sirhan et al. |
| 7,160,258 B2 | 1/2007 | Imran et al. |
| 7,181,261 B2 | 2/2007 | Silver et al. |
| 7,198,603 B2 | 4/2007 | Penner et al. |
| 7,211,045 B2 | 5/2007 | Dala-Krishna et al. |
| 7,273,457 B2 | 9/2007 | Penner |
| 7,283,874 B2 | 10/2007 | Penner |
| 7,308,319 B2 | 12/2007 | Lovett et al. |
| 7,338,512 B2 | 3/2008 | McGuckin, Jr. et al. |
| 7,347,868 B2 | 3/2008 | Burnett et al. |
| 7,392,094 B2 | 6/2008 | Zhang et al. |
| 7,437,193 B2 | 10/2008 | Parramon et al. |
| 7,452,334 B2 | 11/2008 | Gianchandani et al. |
| 7,477,946 B2 | 1/2009 | Tockman et al. |
| 7,555,351 B2 | 6/2009 | Zhang et al. |
| 7,572,228 B2 | 8/2009 | Wolinsky et al. |
| 7,744,542 B2 | 6/2010 | Piaget et al. |
| 7,780,694 B2 | 8/2010 | Palmer et al. |
| 7,801,626 B2 | 9/2010 | Moser |
| 7,850,708 B2 | 12/2010 | Pal |
| 7,890,188 B2 | 2/2011 | Zhang et al. |
| 2002/0045920 A1 | 4/2002 | Thompson |
| 2002/0123672 A1 | 9/2002 | Christophersom et al. |
| 2002/0165601 A1 | 11/2002 | Clerc |
| 2002/0183628 A1 | 12/2002 | Reich et al. |
| 2002/0188207 A1 | 12/2002 | Richter |
| 2003/0114897 A1 | 6/2003 | Von Arx et al. |
| 2003/0139796 A1 | 7/2003 | Sequin et al. |
| 2003/0200031 A1 | 10/2003 | de Kok |
| 2004/0006377 A1 | 1/2004 | Behm |
| 2004/0116992 A1 | 6/2004 | Wardle et al. |
| 2004/0147969 A1 | 7/2004 | Mann et al. |
| 2004/0176672 A1 | 9/2004 | Silver et al. |
| 2004/0204744 A1 | 10/2004 | Penner et al. |
| 2004/0215228 A1 | 10/2004 | Simpson et al. |
| 2005/0080472 A1 | 4/2005 | Atkinson et al. |
| 2005/0096702 A1 | 5/2005 | Denker et al. |
| 2005/0115561 A1 | 6/2005 | Stahmann et al. |
| 2005/0124875 A1 | 6/2005 | Kawano et al. |
| 2005/0136385 A1 | 6/2005 | Mann et al. |
| 2005/0149108 A1 | 7/2005 | Cox |

(56) References Cited

U.S. PATENT DOCUMENTS

| | | |
|---|---|---|
| 2005/0149128 A1 | 7/2005 | Heil, Jr. et al. |
| 2005/0149155 A1 | 7/2005 | Scheiner et al. |
| 2005/0149156 A1 | 7/2005 | Libbus et al. |
| 2005/0165456 A1 | 7/2005 | Mann et al. |
| 2005/0209678 A1 | 9/2005 | Henkes et al. |
| 2005/0245840 A1 | 11/2005 | Christopherson et al. |
| 2006/0009818 A1 | 1/2006 | Von Arx et al. |
| 2006/0047205 A1 | 3/2006 | Ludomirsky et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0079740 A1 | 4/2006 | Silver et al. |
| 2006/0089627 A1 | 4/2006 | Burnett et al. |
| 2006/0089694 A1 | 4/2006 | Zhang et al. |
| 2006/0122522 A1 | 6/2006 | Chavan et al. |
| 2006/0136004 A1 | 6/2006 | Cowan et al. |
| 2006/0142819 A1 | 6/2006 | Penner et al. |
| 2006/0149329 A1 | 7/2006 | Penner |
| 2006/0149330 A1 | 7/2006 | Mann et al. |
| 2006/0178586 A1 | 8/2006 | Dobak, III |
| 2006/0206153 A1 | 9/2006 | Libbus et al. |
| 2006/0241735 A1 | 10/2006 | Tockman et al. |
| 2006/0259085 A1 | 11/2006 | Zhang et al. |
| 2006/0287700 A1 | 12/2006 | White et al. |
| 2006/0293741 A1 | 12/2006 | Johnson et al. |
| 2007/0049833 A1 | 3/2007 | Tearney et al. |
| 2007/0129637 A1 | 6/2007 | Wolinsky et al. |
| 2007/0156126 A1 | 7/2007 | Flaherty |
| 2007/0156205 A1 | 7/2007 | Larson et al. |
| 2007/0162090 A1 | 7/2007 | Penner |
| 2007/0179583 A1 | 8/2007 | Goetzinger et al. |
| 2007/0191904 A1 | 8/2007 | Libbus et al. |
| 2007/0208390 A1 | 9/2007 | Von Arx et al. |
| 2007/0247565 A1 | 10/2007 | Sasiaki et al. |
| 2007/0250126 A1 | 10/2007 | Maile et al. |
| 2007/0274565 A1 | 11/2007 | Penner |
| 2007/0282413 A1 | 12/2007 | Tockman et al. |
| 2007/0282415 A1 | 12/2007 | Tockman et al. |
| 2008/0071178 A1 | 3/2008 | Greenland et al. |
| 2008/0071248 A1 | 3/2008 | Delgado et al. |
| 2008/0071339 A1 | 3/2008 | Stalker et al. |
| 2008/0108904 A1 | 5/2008 | Heil |
| 2008/0176271 A1 | 7/2008 | Silver et al. |
| 2008/0275350 A1 | 11/2008 | Liao et al. |
| 2008/0283066 A1 | 11/2008 | Delgado et al. |
| 2009/0054793 A1 | 2/2009 | Nunez et al. |
| 2009/0171274 A1 | 7/2009 | Harlev et al. |
| 2009/0270742 A1 | 10/2009 | Wolinsky et al. |
| 2010/0016840 A1 | 1/2010 | Stahmann et al. |

FOREIGN PATENT DOCUMENTS

| | | |
|---|---|---|
| EP | 1 068 836 | 1/2001 |
| EP | 1068836 | 1/2001 |
| EP | 1 488 735 | 6/2007 |
| GB | 2 333 044 | 7/1999 |
| JP | H11-089942 | 4/1999 |
| JP | 2000-507142 | 6/2000 |
| JP | 2001-061790 | 3/2001 |
| JP | 2006-500991 | 1/2006 |
| WO | WO 83/03348 | 10/1983 |
| WO | WO 99/34731 | 7/1999 |
| WO | WO 00/16686 | 3/2000 |
| WO | WO 00/59376 | 10/2000 |
| WO | WO 01/67989 | 9/2001 |
| WO | WO 01/87137 | 11/2001 |
| WO | WO 2004/024034 | 3/2004 |
| WO | WO 2004/110263 | 12/2004 |
| WO | WO 2005/058202 | 6/2005 |
| WO | WO 2005/066849 | 7/2005 |
| WO | WO 2005/067817 | 7/2005 |
| WO | WO 2006/062725 | 6/2006 |
| WO | WO 2007/057739 | 5/2007 |
| WO | WO 2007062299 | 5/2007 |
| WO | WO 2007/082115 | 7/2007 |
| WO | 2008002654 | 1/2008 |
| WO | WO 2008/002654 | 1/2008 |
| WO | WO 2008/034077 | 3/2008 |
| WO | WO 2008/057720 | 5/2008 |
| WO | WO 2008/060197 | 5/2008 |
| WO | WO 2008/144191 | 11/2008 |
| WO | 2009006610 | 1/2009 |
| WO | WO 2009/006610 | 1/2009 |

OTHER PUBLICATIONS

International Search Report and Written Opinion issued in PCT/US2010/020756, mailed Sep. 27, 2010.

Invitation to Pay Fees and Partial Search Report issued in PCT/US2010/020756, mailed May 12, 2010.

Goodall, Eleanor V. et al., "Position-Seletive Activation of Peripheral Nerve Fibers with a Cuff Electrode", IEEE Transactions on Biomedical Engineering, IEEE Service Center, Piscataway, NJ, US, vol. 43, No. 8, Aug. 1, 1996.

Holmes et al. "SirolimusEluting Stents vs. Vascular Brachytherapy for InStent Restenosis Within BareMetal Stents" JAMA295 (11): 1264-1273 Mar. 15, 2006.

Lanning & Shandas, "Development and Validation of Implantable Sensors for Monitoring Function of Prosthetic Heart Valves: In Vitro Studies", Medical & Biological Engineering & Computing, Jul. 2003, vol. 41, issue 4, pp. 416-424.

Sheth et al. "Subacute Thrombosis and Vascular Injury Resulting From Slotted-Tube Nitinol and Stainless Steel Stents in a Rabbit Carotid Artery Model" Circulation 1996, 94: 1733-1740.

Stone et al. "Paclitaxel-Eluting Stents vs.Vascular Brachytherapy for In-Stent Restenosis Within Bare-Metal Stents" JAMA 295(11): 1253-1263, Mar. 15, 2006.

Wenaweser et al. "Stent thrombosis following baremetal stent implantation: success of emergency percutaneous coronary intervention and predictors of adverse outcome" European Heart Journal 26: 1180-1187 2005.

International Search Report and Written Opinion from PCT/US2008/062229, mailed Jan. 5, 2009.

* cited by examiner

DEPLOYABLE SENSOR PLATFORM ON THE LEAD SYSTEM OF AN IMPLANTABLE DEVICE

CROSS-REFERENCE TO RELATED APPLICATION

This application claims the benefit under 35 U.S.C. §119 of U.S. Provisional Application No. 61/152,486, filed on Feb. 13, 2009, entitled "DEPLOYABLE SENSOR PLATFORM ON THE LEAD SYSTEM OF AN IMPLANTABLE DEVICE," which is herein incorporated by reference in its entirety.

TECHNICAL FIELD

The present invention relates generally to implantable sensors. More specifically, the present invention relates to implantable sensors and systems and methods for deploying an implantable sensor at a location within a patient's heart or vasculature.

BACKGROUND

Implantable medical devices are often used to treat a variety of medical conditions. Examples of implantable medical devices include drug delivery devices, pain management devices, and devices that treat heart arrhythmias. One example of an implantable medical device used to treat heart arrhythmias is a cardiac pacemaker, which is commonly implanted in a patient to treat bradycardia (i.e., an abnormally slow heart rate). A pacemaker includes a pulse generator and one or more leads, which form electrical connection(s) between the pulse generator and the heart. An implantable cardioverter defibrillator (ICD) may be used to treat tachycardia (i.e., an abnormally rapid heart rate). An ICD also includes a pulse generator and leads that deliver electrical energy to the heart.

Implantable medical devices are also useful in the treatment of heart failure. For example, cardiac resynchronization therapy (CRT) (also commonly referred to as biventricular pacing) is an emerging treatment for heart failure, which involves stimulation of both the right and left ventricles to increase hemodynamic efficiency and cardiac output. In some cases, the treatment of heart failure and heart arrhythmias can be enhanced through the use of implanted sensors. In some systems, for example, a pressure sensor implanted within a chamber of the heart or in a body vessel such as an artery or vein can be used to sense blood pressure, which can be used to compute cardiac output, pulmonary vascular resistance, as well as other hemodynamic parameters. The sensor data from the sensor can be downloaded by a clinician and can be used to modify the therapy delivered by the implantable medical device.

SUMMARY

The present invention relates to implantable sensors and systems and methods for deploying an implantable sensor at a location within a patient's heart or vasculature.

In some embodiments, the present invention is a medical electrical lead. The medical electrical lead includes a lead body having a proximal section adapted to connect to a pulse generator, a distal section, and at least one electrical conductor extending within the lead body. At least one electrode is located on the lead body and is operatively coupled to the at least one electrical conductor. Additionally, the lead includes a resilient cuff frictionally engaged on an outer surface of the lead body; and at least one sensor coupled to the cuff and adapted to detect at least one physiological parameter.

In some embodiments, the present invention is a sensor assembly deployment system for deploying a sensor assembly onto a medical electrical lead. The system includes a delivery catheter having a lumen through which the medical electrical lead is adapted to be delivered. A sensor assembly is coupled to an outer surface of the delivery catheter and includes a resilient cuff and at least one sensor module adapted to detect a physiological parameter. A deployment member is slideably disposed over an outer surface of the delivery catheter and is located proximal to the sensor assembly. In certain embodiments, the deployment system includes an outer catheter having an interior lumen. The delivery catheter including the sensor assembly coupled thereto and deployment member are slideable within the interior lumen of the outer catheter.

In still some embodiments, the present invention is a method of coupling a sensor to an implantable medical electrical lead. An illustrative method includes providing a sensor assembly deployment system including: an outer catheter having an interior lumen; an inner catheter slideably disposed within the interior lumen of the outer catheter; a sensor assembly coupled to an outer surface of the inner catheter, the sensor assembly including a resilient cuff and at least one sensor module; and a deployment member located proximal to the sensor assembly. Additionally, the method includes delivering a medical electrical lead through the interior lumen of the inner catheter to a target location within the heart and securing the lead at the target location within. Next, the deployment member is advanced in a distal direction to deploy the sensor assembly from the inner catheter and onto an outer surface of the lead body. Upon deployment onto the lead body, the sensor assembly frictionally engages the outer surface of the lead body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
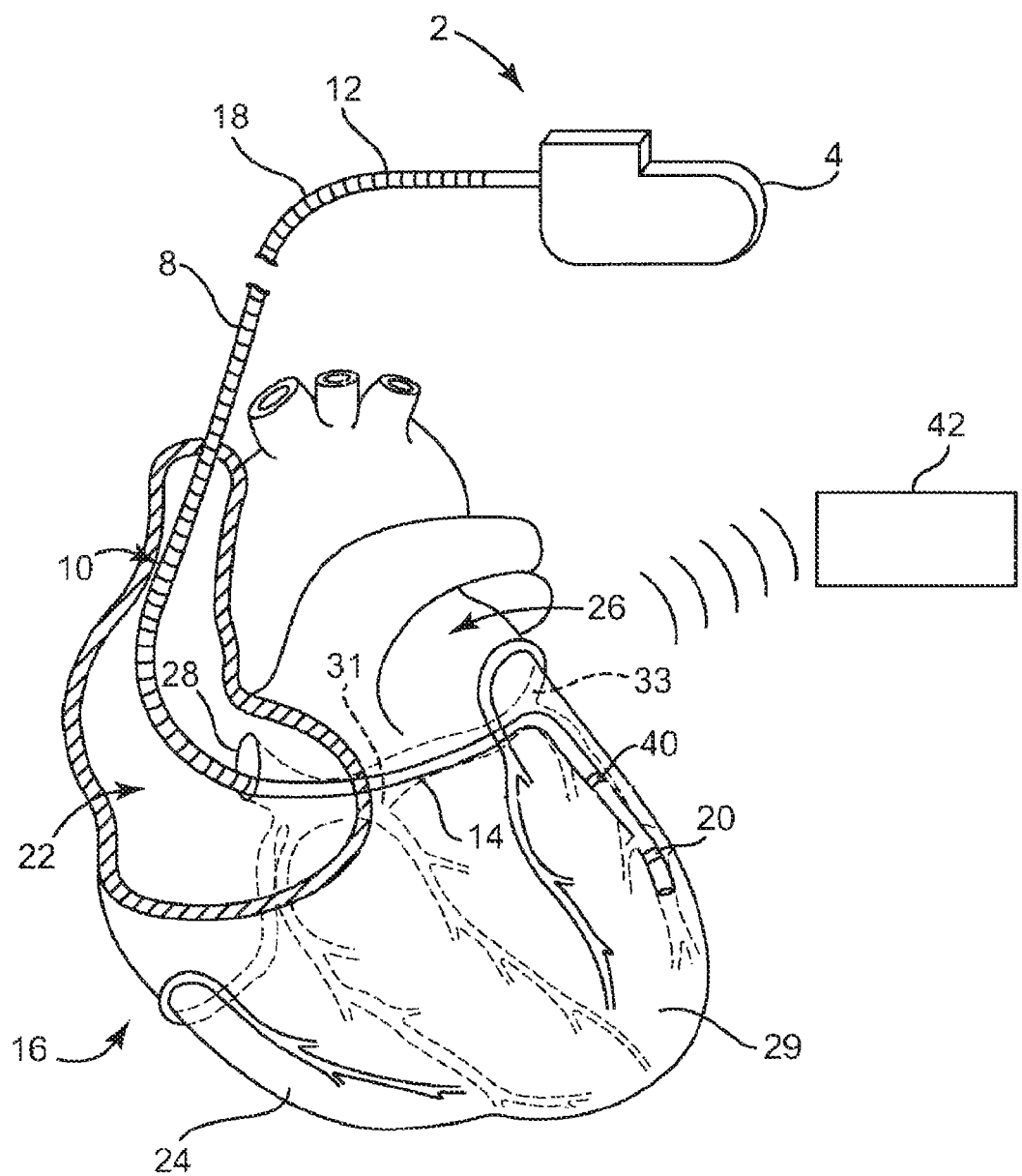
FIG. 1 is a schematic view of a cardiac rhythm management system including a cardiac lead implanted within a patient's heart in accordance with an embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management system 2 including a pulse generator 4 coupled to a lead 8 including a lead body 10 having a proximal section 12 and a distal section 14 deployed within a patient's heart 16. The lead body 10 includes at least one electrical conductor 18 extending within the lead body 10 from the proximal section 12 to the distal section 14. At least one electrode 20 is located on the lead body 10 and is operatively connected to the at least one electrical conductor 18. The heart 16 includes a right atrium 22, a right ventricle 24, a left atrium 26, and a left ventricle 29. The lead 8 can be deployed in a heart chamber, a cardiac vessel, or at some other desired location in the body. In the embodiment illustrated in FIG. 1, the distal section 14 of the lead body 10 is transvenously guided through the right atrium 22, the coronary sinus ostium 28, and into a branch of the coronary sinus 31 or great cardiac vein 33. The illustrated position of the lead body 10 may be used for delivering pacing and/or defibrillation energy to the left side of the heart 16 for the therapeutic treatment of arrhythmias or other cardiac disorders. The position of the lead body 10 may also be used to sense electrical activity occurring within the left side of the heart 16.

According to some embodiments, and as shown in FIG. 1, the cardiac rhythm management system 2 includes a sensor assembly 40 provided on the lead body 10. In some embodiments, the sensor assembly 40 may be delivered and coupled to an existing, implanted lead 8 using a delivery system designed for this purpose. In other embodiments, the sensor assembly 40 is assembled onto the lead body 10 prior to delivery and implantation of the lead 8 within the patient's heart 16. The sensor assembly 40 is delivered along with the lead 8 to a target location within the patient's heart 16 or in a body vessel leading into or from the heart 16. After implantation of the lead 8 at the target location, the position of the sensor assembly 40 may be adjusted to a location that is adequate for detecting the physiological parameter to be monitored and for transmitting information to the pulse generator 4, another device implanted within the body, and/or an external device such as a hand-held monitoring device.

In some embodiments, the data from the sensor assembly 40 can be used to adjust the parameters of the therapy being delivered. For example, the sensor assembly 40 can communicate with the pulse generator 4 via a wired or wireless communication link. The pulse generator 4 is configured to store and/or process the information received from the sensor assembly 40. The data received by the pulse generator 4 can be used to adjust the therapy parameters according to a predetermined therapy protocol. In some embodiments, the sensor assembly 40 may wirelessly transmit sensor data directly to an external device 42. The sensor data received by the external device 42 may be stored and/or downloaded by a physician and used to adjust the therapy as necessary according to the therapy protocol.

Figure 2:
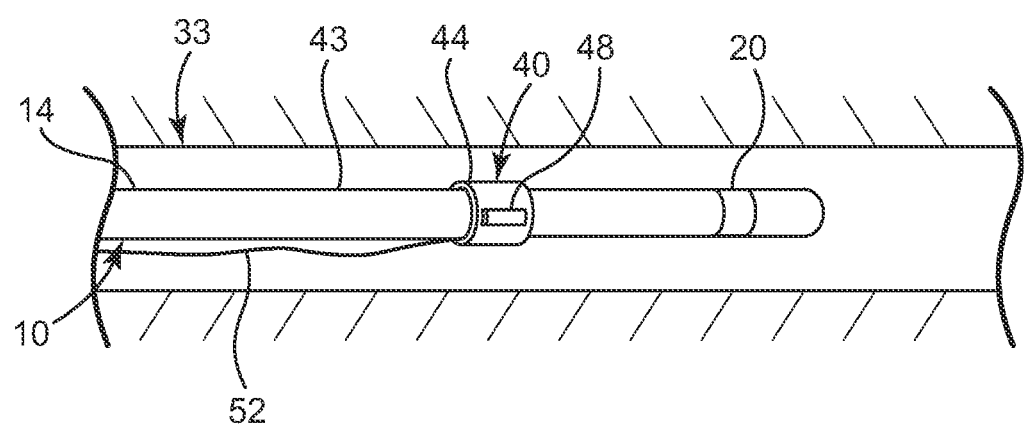
FIG. 2 is a schematic view of a portion of a cardiac lead including a sensor assembly deployed within a vessel according to an illustrative embodiment.

FIG. 2 is a schematic view showing the distal section 14 of the lead body 10 and sensor assembly 40 implanted at a target location located within a cardiac vessel 33. According to one embodiment, as shown in FIG. 2, the implantable sensor assembly 40 can be positioned at a variety of locations over the outer surface 43 of the lead body 10 during the implantation procedure. The implantable sensor assembly 40 includes a sensor platform 44 and a sensor module 48 coupled to the platform 44. In some embodiments, the sensor module 48 is electrically coupled to the pulse generator 4 via an electrical conductor 52 such as an insulated wire. The electrical conductor 52 can be configured to provide an electrical current to power the sensor module 48 as well as to provide a means to transmit and/or receive data back and forth between the sensor 48 and the pulse generator 4. In other embodiments, the sensor module 48 can be a wireless sensor module having a self-contained power supply, and may wirelessly transmit data to the pulse generator 4 and/or an external device.

Figure 3A:
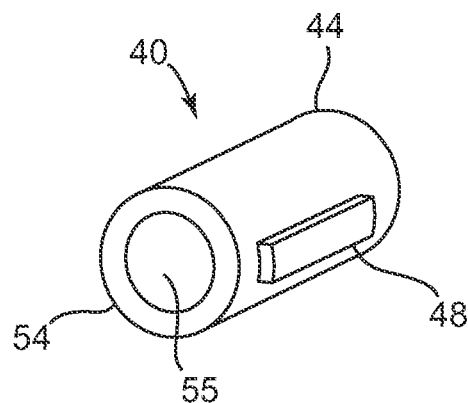
FIG. 3A is a perspective view of a sensor assembly according to an illustrative embodiment.
Figure 3B:
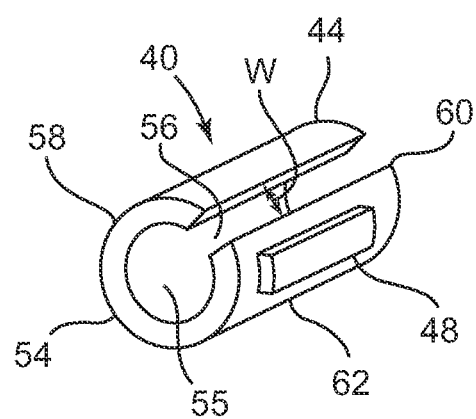
FIG. 3B is a perspective view of a sensor assembly according to another illustrative embodiment.
Figure 4:
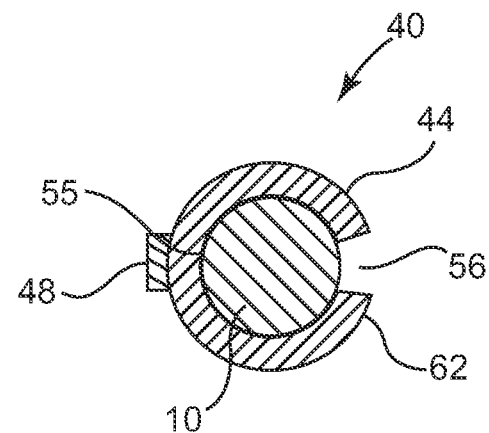
FIG. 4 is an end, cross-sectional view showing the sensor assembly of FIG. 3B coupled to a lead body according to an illustrative embodiment.

FIGS. 3A and 3B are perspective views of the sensor assembly 40 showing the sensor platform 44 and the sensor module 48 in greater detail. FIG. 4 is an end, cross-sectional view showing the sensor platform 44 coupled to the lead body 10. In certain embodiments, and as best shown in FIG. 3A, the sensor platform 44 is a substantially cylindrical resilient cuff 54 having an interior section 55 adapted to frictionally receive a portion of the lead body 10. The lead body 10 is inserted within the interior section 55 of the cuff 54 during coupling of the sensor assembly 40 to the lead body 10. In some embodiments, the cuff 54 is delivered over the exterior of the lead body 10 until a desired location for sensing is reached. Once the desired location has been reached, as further discussed in reference to FIGS. 5A-5C, the cuff 54 is then deployed such that interior section 55 contacts and frictionally engages the exterior of the lead body. According to various embodiments, the inner diameter of the cuff 54 is smaller than an outer diameter of the lead body 10 onto which the sensor assembly 40 is deployed such that the interior section 55 of the cuff 54 frictionally engages the lead body and the sensor assembly 40 is retained in position on the lead body 10 by frictional forces.

In some embodiments, as shown in FIG. 3B, the cylindrical cuff 54 includes a slit 56 extending from a first end 58 to a second end 60 of the cuff 54, which exposes a portion of the cuff 54 to permit the lead body 10 to be inserted within the interior section 55 during coupling of the sensor assembly 40 to the lead body 10. In some embodiments, the width W of the slit 56 is capable of expanding to receive the lead body 10 within the cuff 54 when the sensor assembly 40 is engaged onto the lead body 10. For example, in one embodiment, the width W of the slit 56 is smaller than an outer diameter or width of the lead body 10 and is adapted to expand to a size sufficient to permit the lead body 10 to be inserted into the interior section 55 of the cuff 54.

The cuff 54 can be made of a resilient, pliable material to facilitate insertion of the sensor assembly 40 over the lead body 10 during delivery. Exemplary materials include biocompatible materials such as silicone rubber and polyurethane. In certain embodiments, the cuff 54 may be made of a shape memory alloy or a shape memory polymer. Using a shape memory material such as, for example, Nitinol, allows the cuff 54 to be expanded to permit insertion of a lead body 10 into the interior section of the cuff 54 without permanent deformation of the cuff 54.

According to various embodiments, and as further shown in FIGS. 3A, 3B and 4, the sensor assembly 40 includes at least one sensor module 48. The sensor assembly 40 can include a single sensor module 48 or multiple sensor modules 48. In some embodiments, the sensor assembly 40 can include a first sensor module configured to detect a first physiological parameter and a second sensor module configured to detect a second physiological parameter. Multiple sensor modules configured to detect the same physiological parameter may also be employed. In certain embodiments, the sensor module(s) 48 is/are coupled to an outer surface 62 of the cuff 54. In other embodiments the sensor modules 48 can be embedded into the cuff 54 or mounted to the interior section 55 of the cuff 54. The sensor module 48 can include an electrical conductor that connects to the pulse generator 4, as discussed above in reference to FIG. 2, or can be a wireless sensor module 48.

The sensor module 48 can be configured to detect a variety of physiological parameters. For example, the sensor module 48 can be configured for sensing blood pressure, temperature, blood gas content, strain, fluid flow, chemical properties, electrical properties, magnetic properties, as well as various other physiological parameters. The sensor module 48 can be configured to interact with the implanted pulse generator 4 and transmit data indicative of the physiological parameter being monitored. In some embodiments, the data may be transmitted via the electrical conductor 52 (FIG. 2) to the pulse generator 4, where it may be processed and/or stored until it is accessed by a physician or other caregiver. In other embodiments, the sensor module 48 can be configured to wirelessly transmit the data to the pulse generator 4, to another implanted device, and/or to an external device such as an external computer or hand-held device. In some embodiments, for example, the sensor module 48 can be configured to acoustically transmit data to an external device in a manner described, for example, in U.S. patent application Ser. No. 11/373,005, now U.S. Pat. No. 8,078,278, entitled "Body Attachable Unit In Wireless Communication With Implantable Devices," which is expressly incorporated herein by reference in its entirety for all purposes. Other telemetry modes such as radiofrequency or inductive communication can also be employed for wirelessly communicating with the pulse generator 4, another implanted device, and/or an external device. In some embodiments, the data transmitted by the sensor module 48 can be used to make adjustments to the therapy being delivered. For example, data indicative of the blood pressure in a chamber of the heart 16 can be used to provide closed-loop adjustment of pacing pulses delivered by the pulse generator 4 via the lead 8.

Figure 5A:
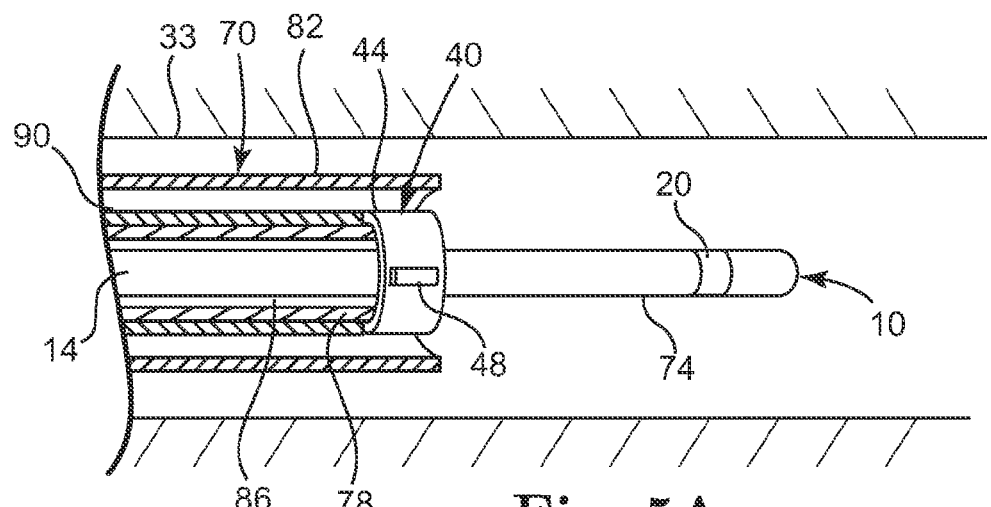
FIGS. 5A and 5B are schematic views of a lead and sensor assembly during delivery of the lead within a vessel according to an illustrative embodiment.
Figure 5B:
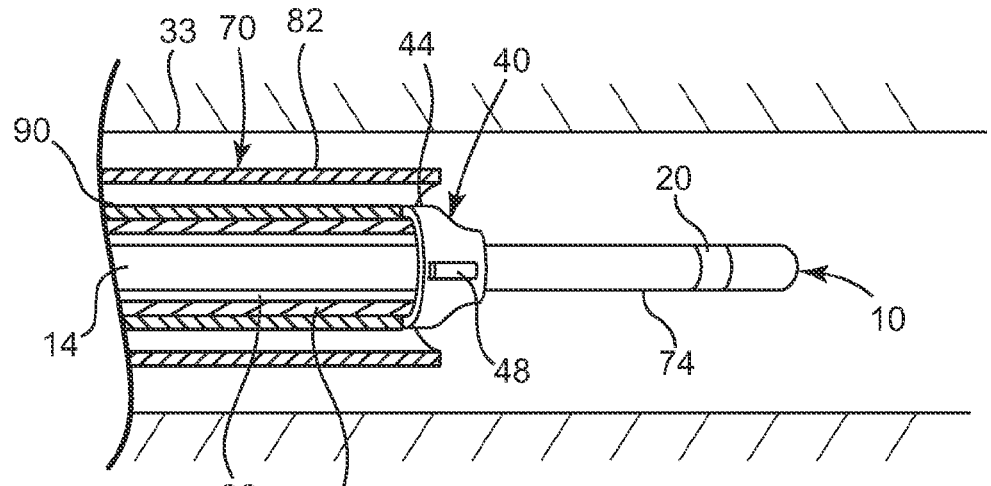
Figure 5C:
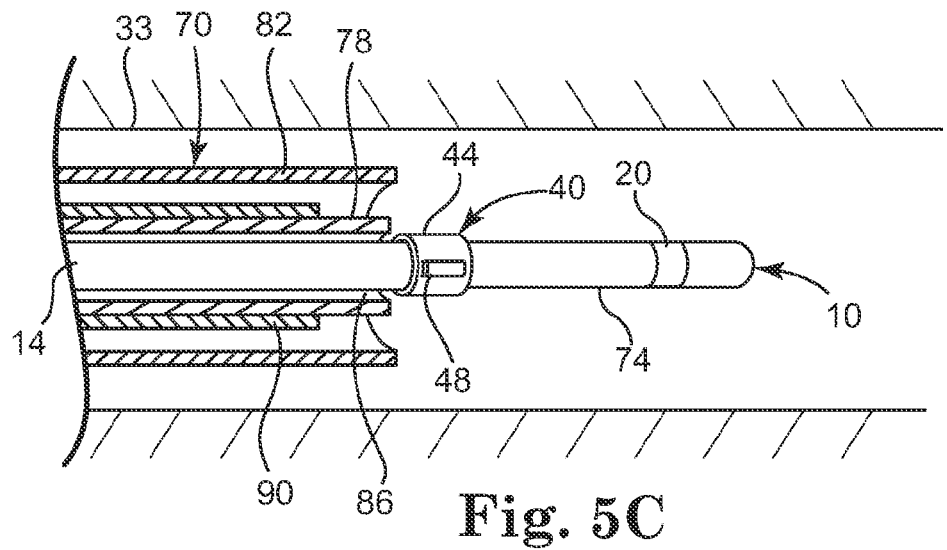
FIG. 5C is a schematic view of the lead and sensor assembly of FIGS. 5A and 5B subsequent to delivery of the sensor assembly over the lead.

FIG. 5A is a schematic view of the distal section 14 of the lead body 10 and the sensor assembly 40 during delivery of the lead 8 to a target location within a vessel 33 and prior to deployment of the sensor assembly 40 onto the lead body 10. FIG. 5B is as schematic view of the distal section 14 of the lead body during deployment of the sensor assembly 40 onto the lead body. FIG. 5C is a schematic view of the distal section 14 of the lead body 10 after deployment of the sensor assembly 40 onto the lead body 10.

According to various embodiments, and as shown in FIGS. 5A-5C, a sensor assembly delivery system 70 is used to couple the sensor assembly 40 including the sensor platform 44 and the sensor module 48 (best shown in FIG. 5C) onto an outer surface 74 of the lead body 10 at a desired location. In certain embodiments, as shown in FIGS. 5A-5C, the sensor assembly delivery system 70 includes an inner catheter 78 slideably disposed within an outer catheter 82. In other embodiments, the inner catheter 78 is utilized during delivery without an outer catheter 82.

The inner catheter 78 includes a lumen 86 though which the lead body 10 can be delivered. Prior to deployment onto the lead body 10, and as shown in FIG. 5A, the sensor assembly 40 is retained on the inner catheter 78 by frictional forces. A deployment member 90, such as a pusher tube or hypotube, may be provided over the inner catheter 78 and is positioned proximal to the sensor assembly 40 to be deployed. In one embodiment, once the lead 8 has been delivered to the target location within the vessel 33, the inner catheter 78 can be moved in either a proximal or distal direction relative to the outer catheter 82 in order to position the sensor assembly 40 at a desired location for sensing. In certain embodiments, the inner catheter 78 may also be rotated to adjust the radial positioning of the sensor assembly 40 prior to deployment. Once the desired location for sensing has been selected, the deployment member 90 can be used to push the sensor assembly 40 in a distal direction off of the inner catheter 78 and onto the lead body 10, as shown in FIG. 5B. In other embodiments, the deployment member 90 can be used to hold the sensor assembly 40 stationary, and the inner catheter 78 is retracted proximally to engage the sensor assembly 40 onto the lead body 10.

Figure 6:
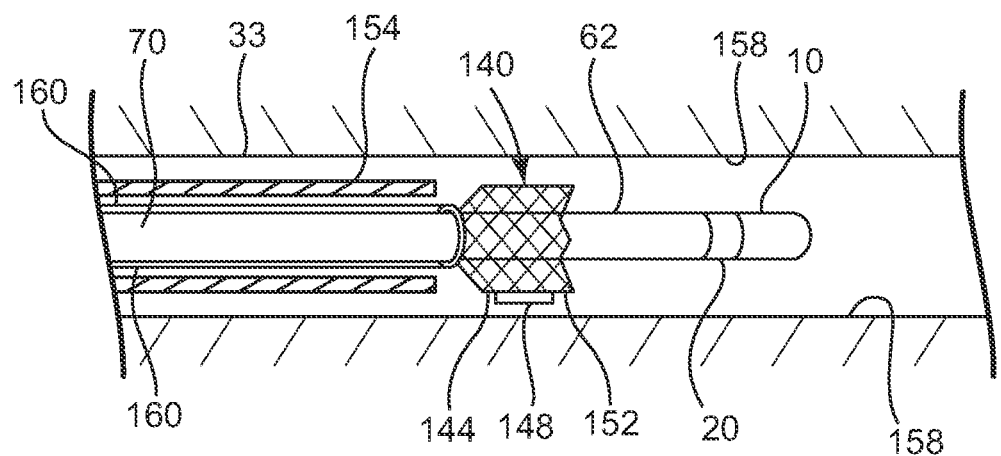
FIG. 6 is a schematic view of a lead and sensor assembly deployed within a vessel according to another embodiment.

FIG. 6 is a schematic view of a portion 70 of a newly implanted lead body 10 deployed within a vessel 33 according to another embodiment. As shown in FIG. 6, a sensor assembly 140 is provided over the outer surface 62 of the newly implanted lead body 10. In the illustrated embodiment, the sensor assembly 140 includes a sensor platform 144 and at least one sensor module 148 coupled to an outer surface 152 of the sensor platform 144. In the illustrated embodiment, the sensor platform 144 is configured to radially expand upon deployment from within the interior of a delivery catheter 154. In some embodiments, and as shown in FIG. 6, the sensor platform 144 may have a stent-like or basket configuration. In other embodiments, the sensor platform 144 may have a coiled configuration or other shape useful for supporting the sensor module 148. During delivery, the sensor assembly 140 is provided over the lead body 10 and is retained in a collapsed configuration by the delivery catheter until deployment. The delivery catheter 154 can be used to advance the lead body 140 to a desired location within the body for implantation. Additionally, the delivery catheter 154 can be used to adjust the position of the sensor assembly 140 at a desired location over the lead body 10. The delivery catheter 154 can be used to adjust the longitudinal position of the sensor assembly 140 over the lead body 10. Additionally, the delivery catheter 154 also may be used to rotate the position of the sensor assembly 140 over the lead body 10. In some embodiments, the delivery catheter 154 can be moved in a proximal direction relative to the lead body 10 to transition the sensor assembly 140 from a collapsed configuration to an expanded configuration. In other embodiments, the sensor assembly 140 may be secured in place on the outer surface 62 of the lead body 10, and the lead body 10 can be moved in a distal direction relative to the catheter 154 to expand the sensor assembly 140.

Unlike stent-like or basket-like fixation devices, the sensor platform 144 illustrated in FIG. 6 does not bear against the vessel walls 158 with a radial expansion force. Rather, the stent-like sensor platform 144 is made from a shape memory material and is configured to expand to an outer diameter that is less than the inner diameter of the vessel 33 so that the sensor module 148 is offset a distance from the vessel wall 158. A number of tether(s) 160 attached to the sensor platform 144 can be used to position the sensor platform 144 at a desired location over the outer surface 62 of the lead body 10. After positioning of the sensor platform 144, the sensor platform 144 is secured in place over the outer surface 62 of the lead body 10 by securing the tethers 160 to the proximal section 12 of the lead body 10. With the tether(s) 160 secured to the proximal section 12 of the lead body 10, the sensor platform 144 can be retained in place at a desired location on the lead body 10. In some embodiments, the tether(s) 160 may also be used as an electrical conduit for providing power to the sensor module 148 and for transmitting data signals back and forth between the sensor module 148 and the pulse generator 4. According to other embodiments, the stent-like sensor platform 144 may be retained in place on the lead body 10 by one or more stop features provided on the lead body 10, as more fully described in U.S. application Ser. No. 11/114,730, now U.S. Pat. No. 7,477,946, entitled "Fixation Device for Coronary Venous Lead," which is expressly incorporated herein by reference in its entirety for all purposes.

Figure 7:
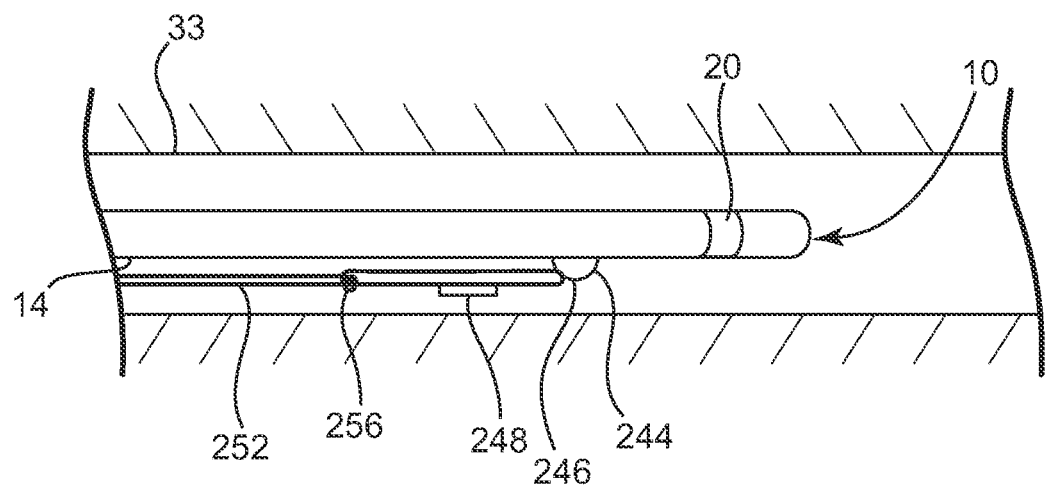
FIG. 7 is a schematic view of a lead and sensor assembly deployed within a vessel according to another embodiment.

FIG. 7 is a schematic view of a distal section 14 of a newly implanted lead body 10 and sensor assembly 244 deployed within a vessel 33 according to another embodiment. As shown in FIG. 7, a sensor assembly 244 includes an eyelet or loop 246 coupled to the lead body 10, which in some embodiments, may further serve as a guidewire management feature. A guidewire management feature facilitates and guides the insertion of a guidewire used during the implant procedure to traverse the body. In other embodiments, the sensor assembly 244 can be configured as a collar which encompasses the circumference of the lead body 10.

As shown in FIG. 7, the sensor module 248 is attached to a tether 252 which can be pre-threaded through the eyelet or loop 246 of the sensor assembly 244 prior to delivery of the lead body 10 within the patient's heart. In some embodiments, the tether 252 may comprise an insulated wire which, in addition to facilitating the delivery of the sensor module 248 onto the lead body 10, can be used to provide power to the sensor assembly 244 and to transmit data back and forth from the sensor module 248 to the pulse generator 4. In one embodiment, and as further shown in FIG. 7, the tether 252 can be configured with a slip-knot like feature 256 that can be secured to the eyelet or loop 246 using tension once the sensor module 248 has been delivered to a desired location along the length of the lead body 10. The tether 252 can be fabricated from suture string or thin, biocompatible wire. In some embodiments, the tether 252 can be the sensor lead used to transmit power to the sensor and convey data back and forth to and from the sensor module 248 and the pulse generator 4.

The lead body 10 can be delivered to the target location within the patient's heart using a stylet, catheter, or other suitable delivery device. Once the lead body 10 has been implanted at the target location within the patient's heart or in a body vessel leading to or from the heart, the position of the sensor module 248 can be adjusted by pulling on one end of the tether 252. Once a desired position for the sensor module has been identified, the tether 252 can be secured at the proximal end 12 of the lead body 10.

In certain embodiments, a sensor assembly such as described above according to the various embodiments can also be deployed onto an existing, implanted lead. For example, in one embodiment, a method of deploying a sensor assembly onto an existing implanted lead includes guiding a sensor deployment system to a location adjacent the existing implanted lead located within a patient's heart, engaging the lead body, and deploying a sensor assembly including at least a sensor module onto the lead body.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A medical electrical lead configured for deployment within a vessel of a cardiovascular system, comprising:
    a lead body having a proximal section and a distal section, the proximal section of the lead body adapted to connect to a pulse generator;
    at least one electrical conductor extending within the lead body;
    at least one electrode located on the lead body and operatively coupled to the at least one electrical conductor;
    a resilient cuff sized and configured for frictional engagement with an outer surface of the lead body, the resilient cuff adapted to be disposed circumferentially about the lead body when the lead and the resilient cuff are deployed within the vessel; and
    at least one sensor module coupled to the cuff such that the sensor module is disposed in the vessel when the lead is disposed in the vessel, the at least one sensor module including a sensor adapted to detect at least one physiological parameter from within the vessel.

2. The lead according to claim 1, wherein the sensor module further comprises an electrical conductor adapted to connect to the pulse generator.

3. The lead according to claim 1, wherein the sensor is a wireless sensor and is adapted to communicate wirelessly to an external device.

4. The lead according to claim 1, wherein the sensor is a wireless sensor and is adapted to communicate wirelessly with a pulse generator.

5. The lead according to claim 1, wherein the at least one physiological parameter is selected from the group of parameters including blood pressure, temperature, blood gas content, strain, or fluid flow.

6. The lead according to claim 1, wherein the at least one physiological parameter includes blood pressure.

7. The lead according to claim 1, wherein the sensor module comprises a first sensor adapted to detect a first physiological parameter and a second sensor adapted to detect a second physiological parameter.

8. The lead according to claim 1, wherein the cuff includes a slit extending from a first end of the cuff to a second end of the cuff, the slit comprising a width W smaller than an outer diameter of the lead body, the slit configured to expand such that the cuff width increases to a size sufficient to receive the lead body within an interior section of the cuff.

9. The lead according to claim 1, wherein an inner diameter of the cuff is smaller than an outer diameter of the lead body.

10. The lead according to claim 1, wherein the cuff comprises a shape memory material.

11. A medical electrical lead configured for deployment within a cardiac vessel, comprising:
    a lead body having a proximal section and a distal section, the proximal section of the lead body adapted to connect to a pulse generator;
    at least one electrical conductor extending within the lead body;
    at least one electrode located on the lead body and operatively coupled to the at least one electrical conductor;
    a resilient cuff configured for frictional engagement with the outer surface of the lead body, the resilient cuff adapted to be disposed circumferentially about the lead body when the lead and the resilient cuff are deployed within the cardiac vessel; and
    at least one sensor module coupled to the cuff such that the sensor module is disposed in the vessel when the lead is disposed in the vessel, the at least one sensor module including a sensor adapted to detect at least one physiological parameter from within the vessel;

wherein the sensor is a wireless sensor and is adapted to communicate wirelessly to an external device.

12. The lead according to claim 11, wherein the wireless sensor is further adapted to communicate wirelessly with a pulse generator.

13. The lead according to claim 11, wherein the at least one physiological parameter is selected from the group of parameters including blood pressure, temperature, blood gas content, strain, or fluid flow.

14. The lead according to claim 13, wherein the at least one physiological parameter includes blood pressure.

15. The lead according to claim 11, wherein the sensor module comprises a first sensor adapted to detect a first physiological parameter and a second sensor adapted to detect a second physiological parameter.

16. The lead according to claim 11, wherein the cuff includes a slit extending from a first end of the cuff to a second end of the cuff, the slit comprising a width W smaller than an outer diameter of the lead body, the slit configured to expand such that the cuff width increases to a size sufficient to receive the lead body within an interior section of the cuff.

17. The lead according to claim 11, wherein an inner diameter of the cuff is smaller than an outer diameter of the lead body.

18. The lead according to claim 11, wherein the cuff comprises a shape memory material.

* * * * *